(12) United States Patent
Dos Santos Redinha (10) Patent No.: US 10,695,144 B2
(45) Date of Patent: Jun. 30, 2020

(54) THREE-DIMENSIONAL MARKERS FOR AXIOGRAPHY AND INDIVIDUAL VALUES DETERMINATION

(71) Applicant: Luís António Dos Santos Redinha, Paco de Arcos (PT)

(72) Inventor: Luís António Dos Santos Redinha, Paco de Arcos (PT)

( * ) Notice: Subject to any disclaimer, the term of this patent is extended or adjusted under 35 U.S.C. 154(b) by 0 days.

(21) Appl. No.: 15/515,607

(22) PCT Filed: Oct. 6, 2015

(86) PCT No.: PCT/IB2015/057631
§ 371 (c)(1),
(2) Date: Mar. 30, 2017

(87) PCT Pub. No.: WO2016/055932
PCT Pub. Date: Apr. 14, 2016

(65) Prior Publication Data
US 2017/0296296 A1    Oct. 19, 2017

(30) Foreign Application Priority Data
Oct. 7, 2014 (PT) .......................................... 107944

(51) Int. Cl.
*A61B 90/00* (2016.01)
*A61C 19/045* (2006.01)
*A61C 9/00* (2006.01)

(52) U.S. Cl.
CPC ............ *A61B 90/39* (2016.02); *A61C 9/0046* (2013.01); *A61C 19/045* (2013.01); *A61B 2090/3912* (2016.02); *A61B 2090/3916* (2016.02)

(58) Field of Classification Search
CPC ... A61C 9/0046; A61C 19/045; A61C 9/0045; A61B 90/39; A91B 2090/3912; A91B 2090/3916
See application file for complete search history.

(56) References Cited

U.S. PATENT DOCUMENTS 4,034,474 A * 7/1977 Lee ...................... A61C 11/022
433/69
4,034,475 A * 7/1977 Lee ...................... A61C 11/022
433/214

(Continued)

FOREIGN PATENT DOCUMENTS

EP      2011449 A1   1/2009
WO   2012100203 A2   7/2012

*Primary Examiner* — Cris L. Rodriguez
*Assistant Examiner* — Hao D Mai
(74) *Attorney, Agent, or Firm* — Mark M. Friedman (57) ABSTRACT

A set of three-dimensional markers enables accurate transfer of scanned dental information from an intra-oral scanner to a virtual articulator, for axis transposition in axiography and for accurate determination of individual values, such as Bennett and condylar guidance angles. The set of three-dimensional markers includes a first marker, which is aligned with a buccal face of an upper incisor, and a second marker, which is positioned outside buccal surfaces of the teeth. The first marker consists of three elements which fit together in a number of different combinations to form a single piece. For edentulous patients, a third marker and a spacer element are provided.

5 Claims, 14 Drawing Sheets

(56) References Cited

U.S. PATENT DOCUMENTS

| | | | |
|---|---|---|---|
| 4,270,901 A * | 6/1981 | Comparetto | A61C 19/045 |
| | | | 433/54 |
| 4,602,905 A | 7/1986 | O'Keefe | |
| 5,230,623 A * | 7/1993 | Guthrie | G06F 3/0346 |
| | | | 33/513 |
| 5,280,427 A * | 1/1994 | Magnusson | A61B 90/11 |
| | | | 600/407 |
| 2005/0070782 A1* | 3/2005 | Brodkin | A61C 13/0004 |
| | | | 600/407 |
| 2011/0045432 A1* | 2/2011 | Groscurth | A61C 1/084 |
| | | | 433/75 |
| 2012/0107763 A1* | 5/2012 | Adams | A61B 1/24 |
| | | | 433/29 |
| 2013/0023797 A1* | 1/2013 | Hanewinkel | A61B 5/1076 |
| | | | 600/590 |
| 2014/0287379 A1 | 9/2014 | Chun et al. | |

* cited by examiner

THREE-DIMENSIONAL MARKERS FOR AXIOGRAPHY AND INDIVIDUAL VALUES DETERMINATION

FIELD OF THE INVENTION

This invention was created within the scope of mechanical engineering with application in dentistry. In the international classification of patents this belongs to the A61C13, A61C9 and A61F5 sections.

STATE OF THE ART

In the last decade, the evolution of dental manufacturing methods using CAD-CAM systems has become widespread. The possibility of combining a virtual articulator system with modelling software allows greater control and ease of implementation of prosthetic pieces. However, the information transfer systems that are currently used still require the use of a face-bow or axiographer and records with physical mounted models in a conventional articulator. Moreover, its subsequent scanning needs the use of a high cost laboratory scanner. Likewise, the determination of individual values (condylar guidance angle and Bennett angle), involves the realization of conventional intraoral records and their reading in a conventional articulator.

In the last years, intra-oral scanners have been used more in dental offices, which motivated the creation of this invention. This concerns a set of three-dimensional markers that should be included in the scanning protocol, that together with the dental arches scanned information allows the transposition to the virtual articulator, of axiography and individual values determination for virtual articulators. The scanned information is acquired through intraoral scanner, which transfers the information from the physical mounted models to the virtual environment.

BRIEF SUMMARY OF THE INVENTION

For a better understanding of the invention, it becomes necessary to detail its application, that is, to describe the axiography methods and the individual values determination.

Figure 1:
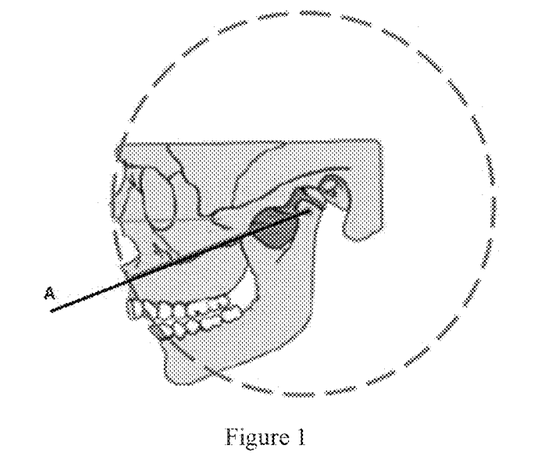
FIG. 1—Representation of the spatial localization of mandible/skull relatively to the pure rotation axis (A).
Figure 2:
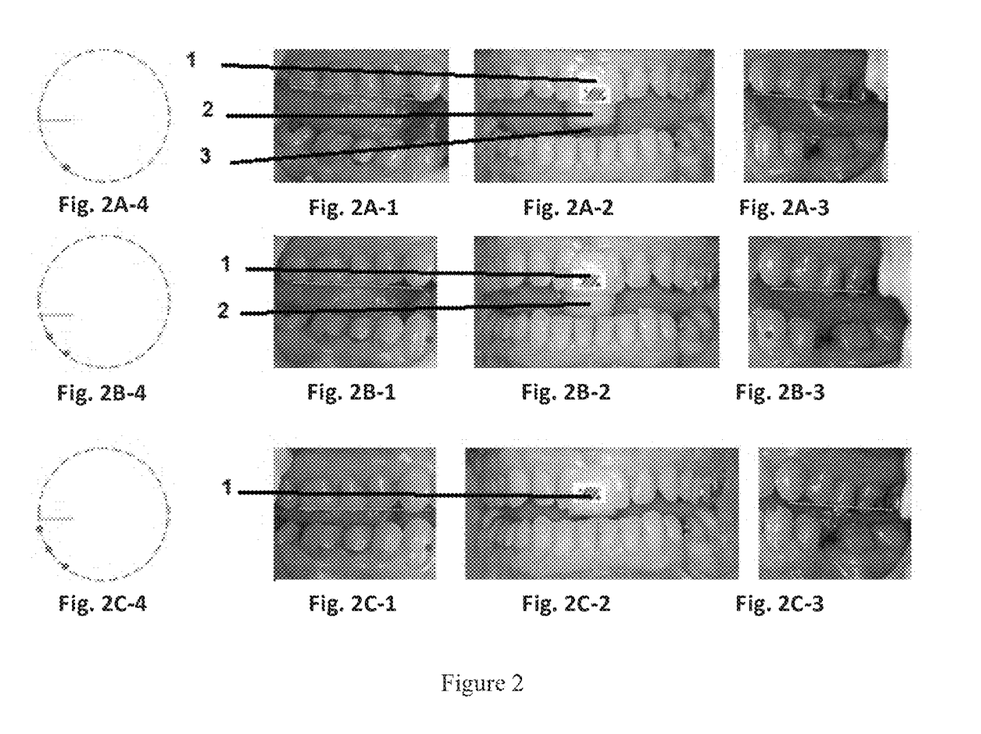
FIG. 2—Measurement of the three vertical dimensions.

The first step is the determination of the pure rotational axis—axiography—of the temporomandibular joint (TMJ), which is achieved with the use of an intraoral scanner. With regard to FIG. 1 is possible to observe the pure rotational axis.

The biomechanics of the temporomandibular joints (TMJ) allows the clinical determination of a hinge or rotational axis that remains constant in the first phase of mouth opening up to approximately 15 to 20 mm. The contact point of the lower incisors with an anterior horizontal platform placed in the interincisal zone of the upper jaw, when the condyles are in a musculoskeletally stable position, is the reference point of the closing arch in pure rotation of the TMJ at a given vertical dimension.

By registering the intermaxillary intraoral relationship at three consecutive pre-set vertical dimensions, it is possible to determine the closure arch in pure rotation and, therefore, to determine the spatial position of the mandible hinge axis.

The vertical dimensions of occlusion used as a reference to locate the mandibular closure arch, are obtained using the markers purposed in this invention. The set of markers includes:
marker (4) which has three parts: upper element (1), intermediate element (2) and lower element (3), that fit together to create a single piece (4) or the elements (19) (17) (18) respectively, in case of edentulous patients where stability of the attachment is harder to achieve;
markers (5) (26), which are solely for determination of individual values.

To better understand the measurement of the three vertical dimensions using this invention and to explain its technical effect, the measurements procedures are described:
the three vertical dimensions of occlusion are obtained by using the first set of markers. These markers are stabilized in the upper interincisal middle line using a quick-setting material (wax, impression compound or elastomers) and aligned so that its lower flat surface is in the horizontal plane. This way the relative position of the dental arches is scanned through the relationship between a reference point of the lower jaw (circular dot) and the upper occlusal plane (dashed line), when there is contact between the lower incisors and the marker in the most retruded position of the mandible (FIGS. 2A-1 through 2A-4). After removal of the lower element (3) the second measurement is achieved (FIGS. 2B-1 through 2B-4). The third vertical dimension is obtained after removing the intermediate element (2) (FIGS. 2C-1 through 2C-4). It should be noted that all three measurements are performed using the intraoral scanner;
in fact, scanning the intraoral references allows to determine not only the spatial localization of the upper arch but also the closure arch from a controlled movement of a reference point of the lower arch and, therefore, the pure rotational axis of the mandible.

In addition, the fully assembled set does not exceed 15 to 20 mm of mouth opening. The elements (2) (3), which are withdrawable, are about 3 mm thick and the element (1) is 1 mm thickness in the thinnest part.

After that a second step is required since it is mandatory to define a third reference point which will complete the information needed to finish the face-bow recording. Transferring the conventional face-bow information requires the determination of the rotational axis of the mandible (real or average) and a third reference point, which relates the maxillary occlusal plane with the anatomical references of the skull base. The setting of the virtual face-bow requires the scan of the incisive papilla, which has a direct anatomical relationship with the incisive fossa and it will be the third reference point of the spatial location of the upper jaw.

Figure 3:
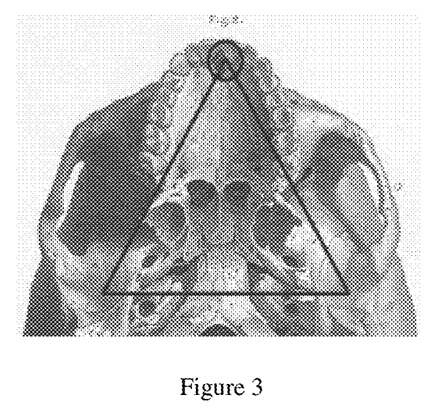
FIG. 3—Definition of an anatomical plane.

According to Westesson, it is the TMJ joint concentricity that allows the pure rotation movement. This movement occurs in the upper anterior quadrant that results from the intersection of the horizontal line passing through the base of the temporal bone and the vertical line passing through the uppermost point of the glenoid fossa. The connection of these two joint points (which coincide to TMJ condyles position throughout its pure rotational movement), with the incisive fossa point define an anatomical plane (Sanz-Redinha Plane)—FIG. 3.

Figure 4:
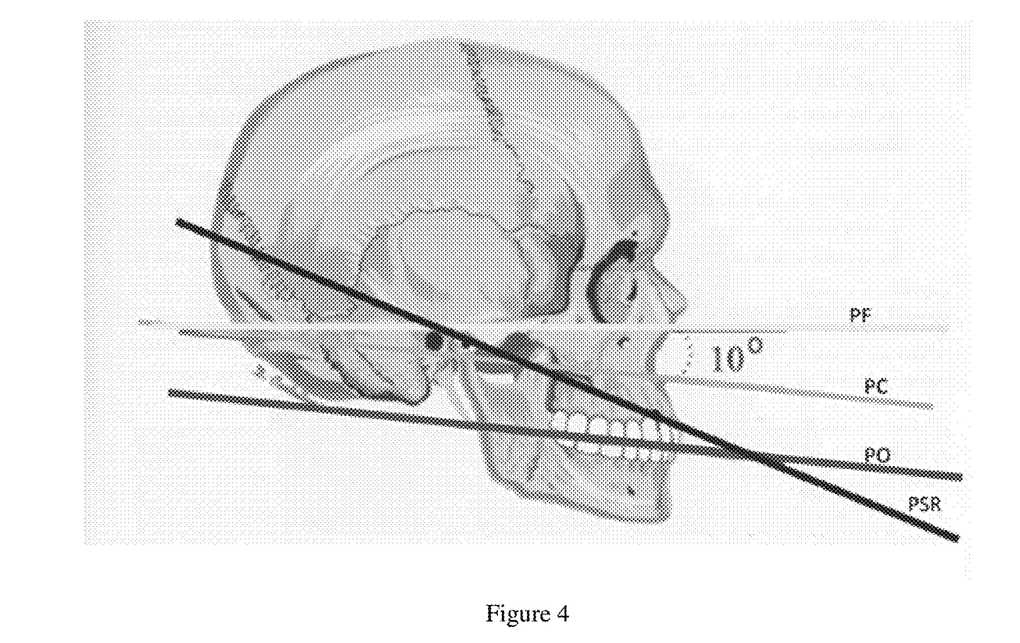
FIG. 4—Representation of virtual positioning of the upper jaw relative to the most used anatomical planes: PF—Frankfurt Plane; PC—Camper Plane; PSR—Sanz-Redinha Plane and PO—Occlusion Plane.

By virtually determining the Sanz-Redinha Plane, which includes the pure rotation axis of the mandible and a reliable bone reference in the upper jaw (incisive fossa), it is possible to virtually position the upper jaw relative to the most used anatomical planes in mounting models articulated with conventional face-bows (Frankfurt and Camper Planes)—FIG. 4.

Figure 5:
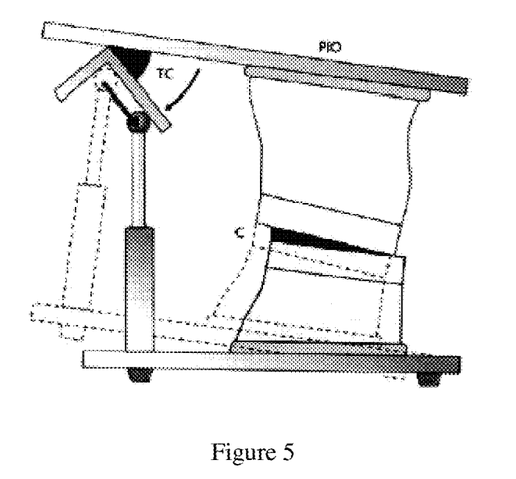
FIG. 5—Representation of the condylar inclination.
Figure 6:
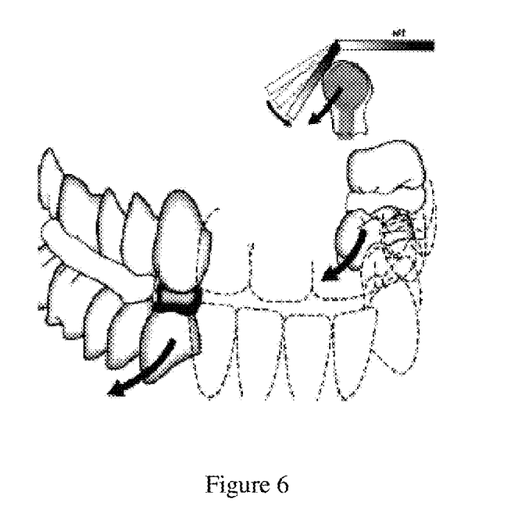
FIG. 6—Representation of Bennett angles.

Without using complex pantography techniques, determining individual values through mounted models in articulator is restricted to estimated values of the condylar inclination (FIG. 5) and Bennett angles (FIG. 6). This is achieved by performing intermaxillary records in protrusion edge to edge positions and left and right laterotrusive movements.

Therefore, having the mandible pure rotational axis determined in advance, as it was mentioned before, the intraoral dental references digitization in this edge to edge positions allows the virtual setting of individualized values of condylar angle and Bennett angles.

For individual values scanning the marker (5) is used, stabilizing the relative positions of the dental arches through the use of waxes, impression compound or quick-set elastomeric material (vinyl polysiloxane or polyether).

Figures 7, 7A, 7A, 7B, 7B, 7C, 7C:
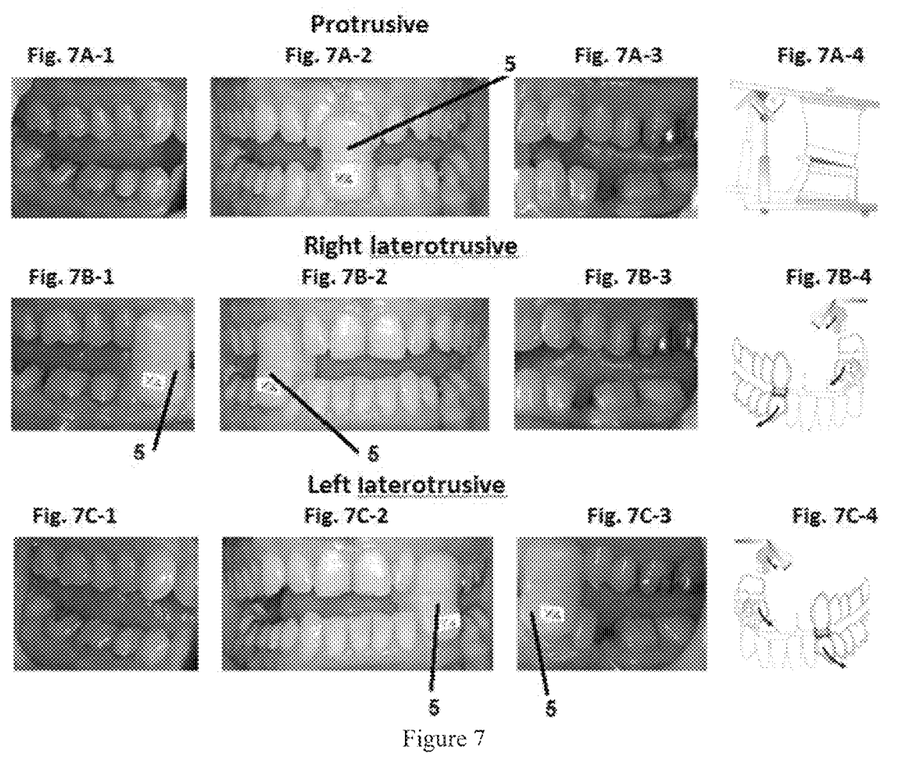
FIG. 7—Measurement of protrusive (FIGS. 7A-1 through 7A-4), right (FIGS. 7B-1 through 7B-4) and left (FIGS. 7C-1 through 7C-4) laterotrusive movements, with the marker (5).
Figure 8:
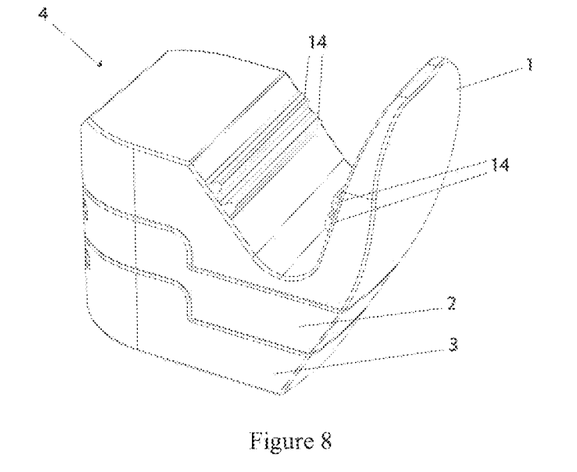
FIG. 8—Marker (4) with all its elements (1) (2) (3) attached where a slot formed by two ridges (14) can be seen.
Figure 9:
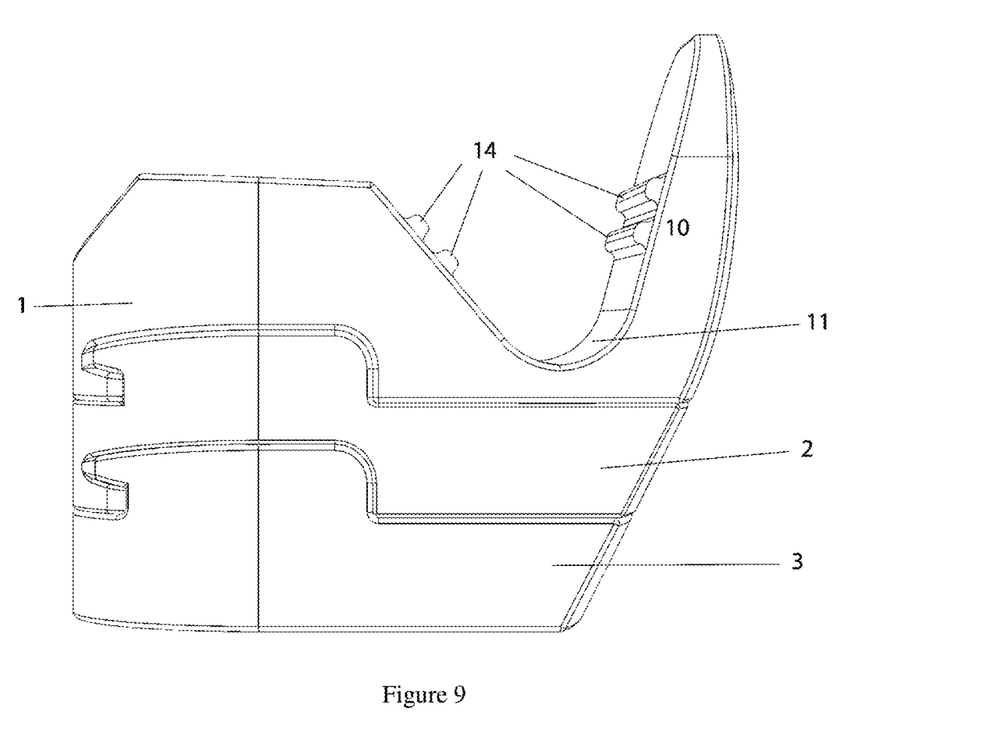
FIG. 9—Marker (4) with all its elements (1) (2) (3) attached where a slot formed by two ridges (14) (14) can be seen.
Figure 10:
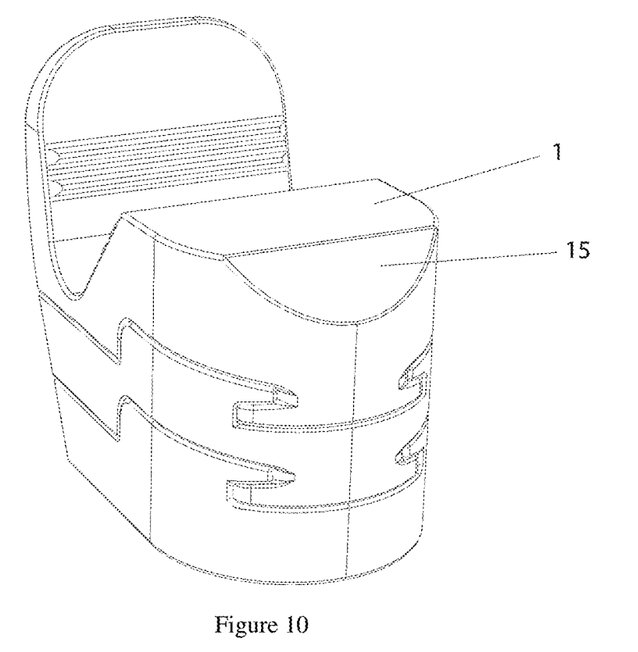
FIG. 10—Marker (4) with all its elements (1) (2) (3) attached where a slot formed by two ridges (14) (14) and cut (15) are visible.
Figure 11:
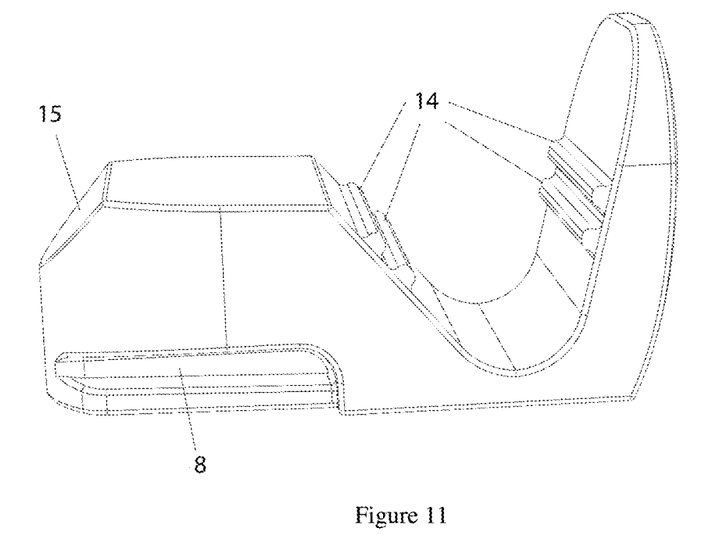
FIG. 11—Element (1) where cut (15), slots (14) and hollows (9) can be seen. Hollow (8) is identical to hollow (9) on the symmetrical side of the element (1).
Figure 12:
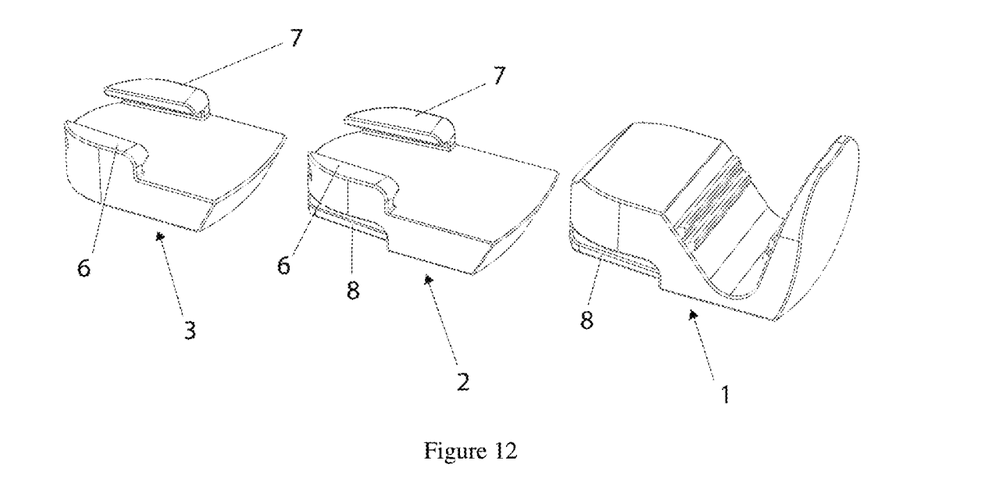
FIG. 12—Element (4) where elements (1) (2) (3) can be observed separately. Hollows (9) and projections (7) (6) that allow the attachment of various elements are visible. Hollow (8) is identical to (9) on the symmetrical side of the element (1), that is, on same side of projection (7).
Figure 13:
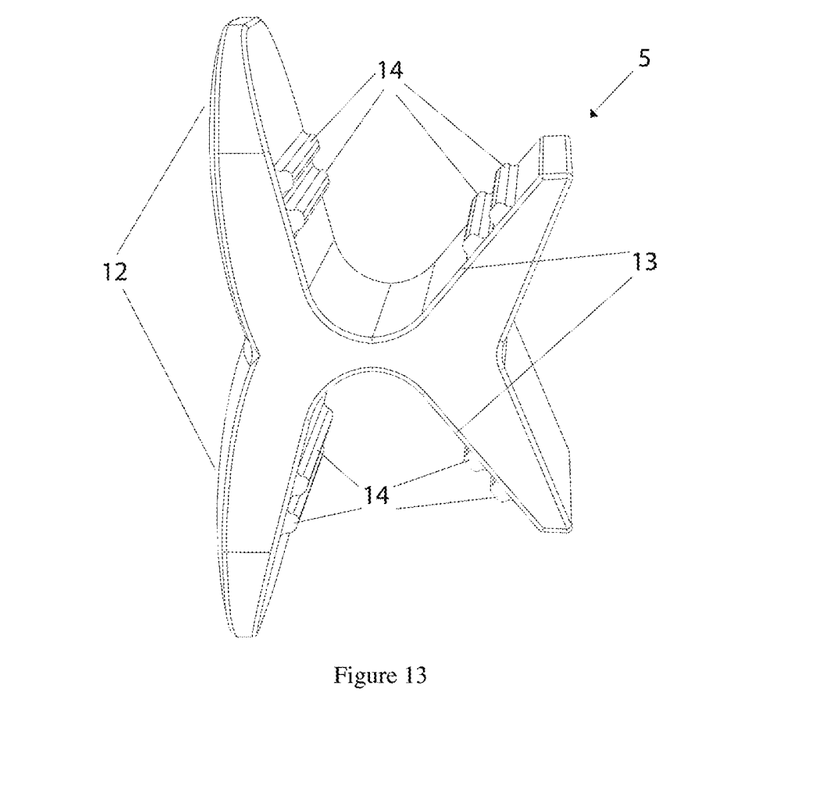
FIG. 13—Marker (5) with projection (12), cavity (13) and a slot formed by two ridges (14).
Figure 14:
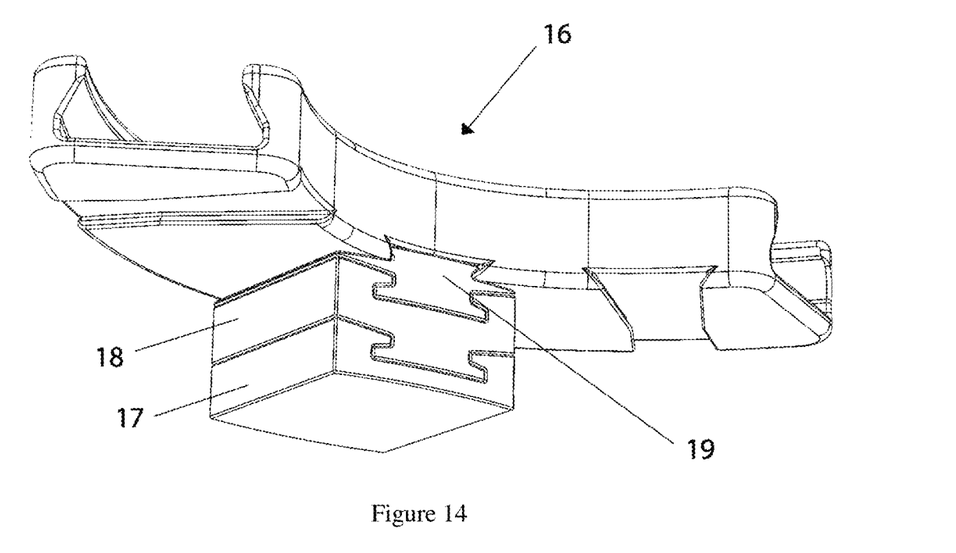
FIG. 14—Inside view of spacer (16) in upper position with elements (17) (18) (19) fitted in central position.
Figure 15:
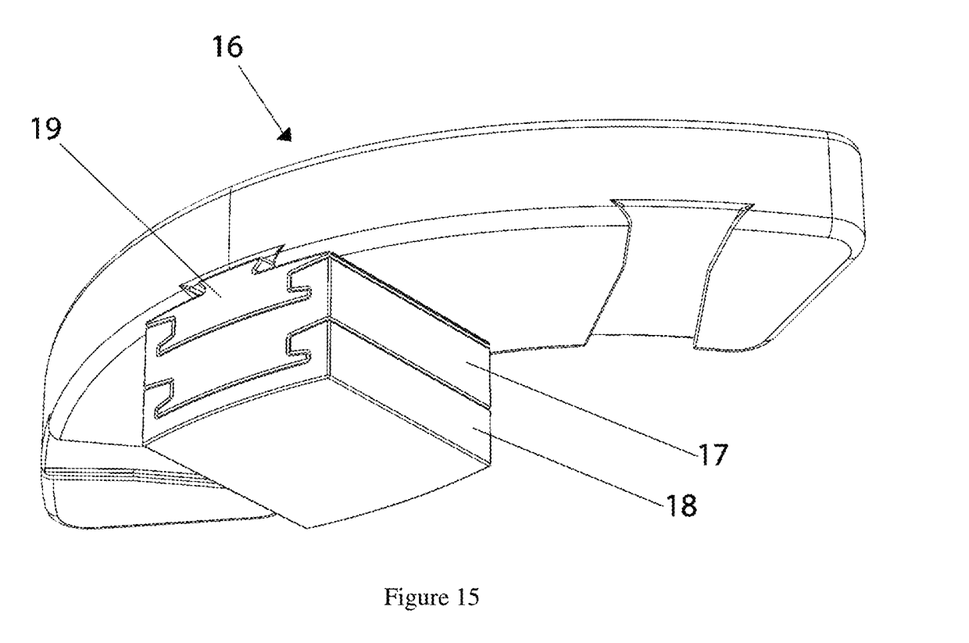
FIG. 15—Outside view of spacer (16) in upper position, with elements (17) (18) (19) fitted in central position.
Figure 16:
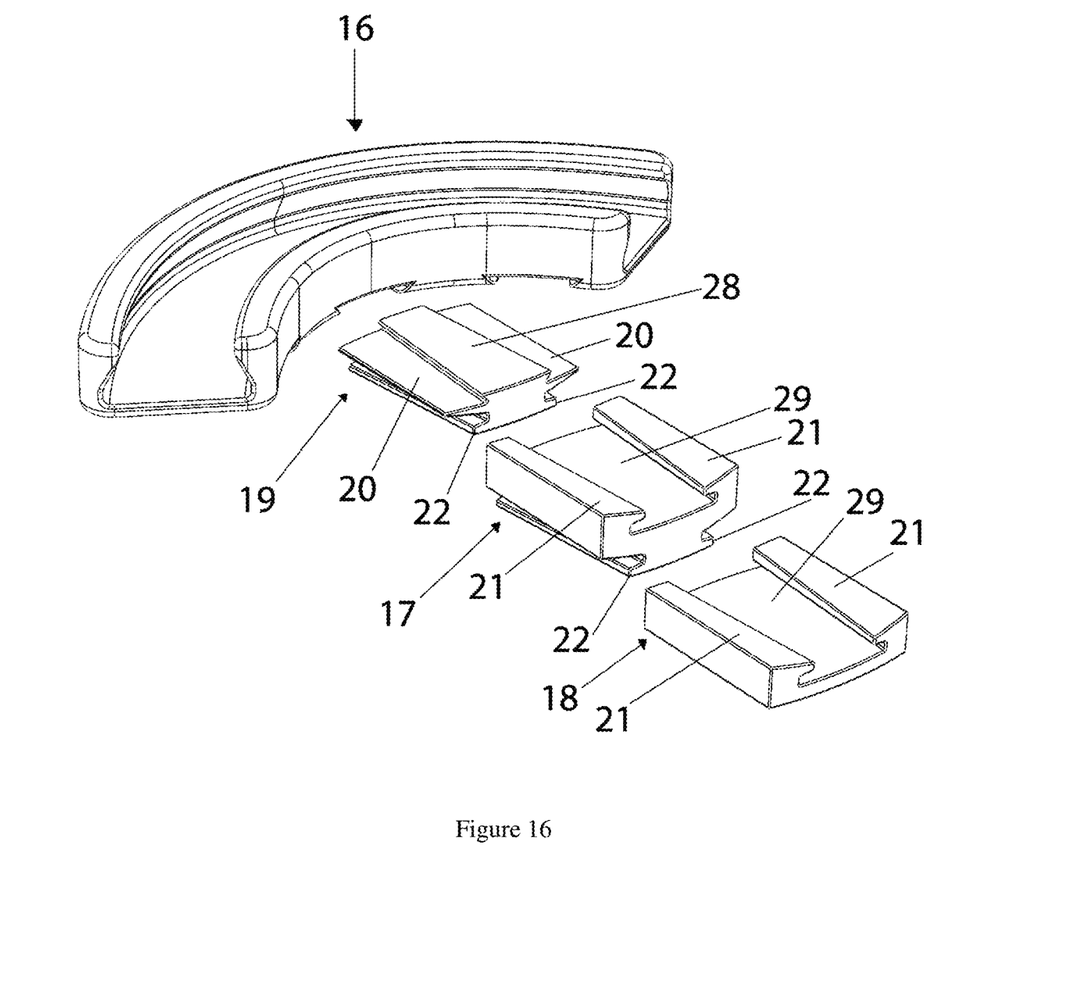
FIG. 16—Spacer (16) in upper position where elements (17) (18) (19) can be seen separately and projections (20) (21) and slots (22) are visible.
Figure 17:
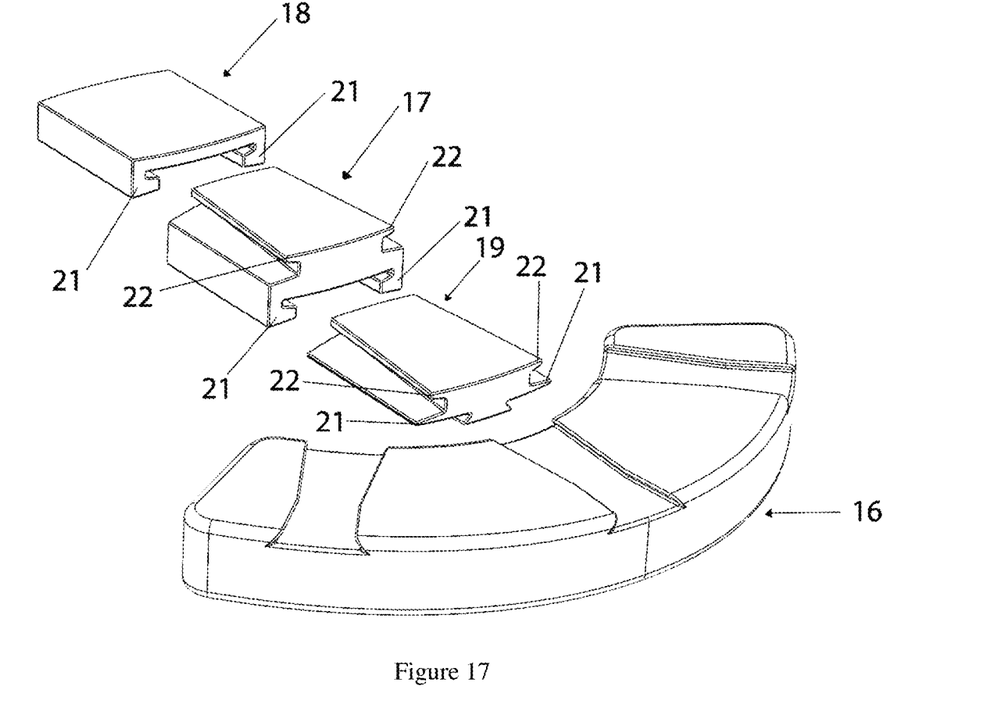
FIG. 17—Spacer (16) in bottom position where elements (17) (18) (19) can be seen individually and projections (20)(21) and slots (22) are visible.
Figure 18:
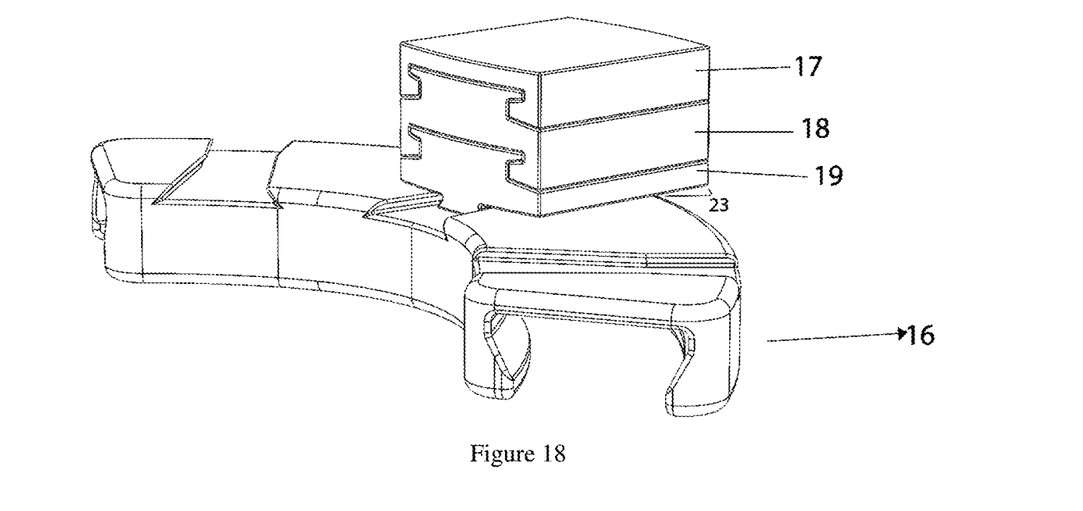
FIG. 18—Inside view of spacer (16) in bottom position with elements (17) (18) (19) fitted in central position showing projection (23).
Figure 19:
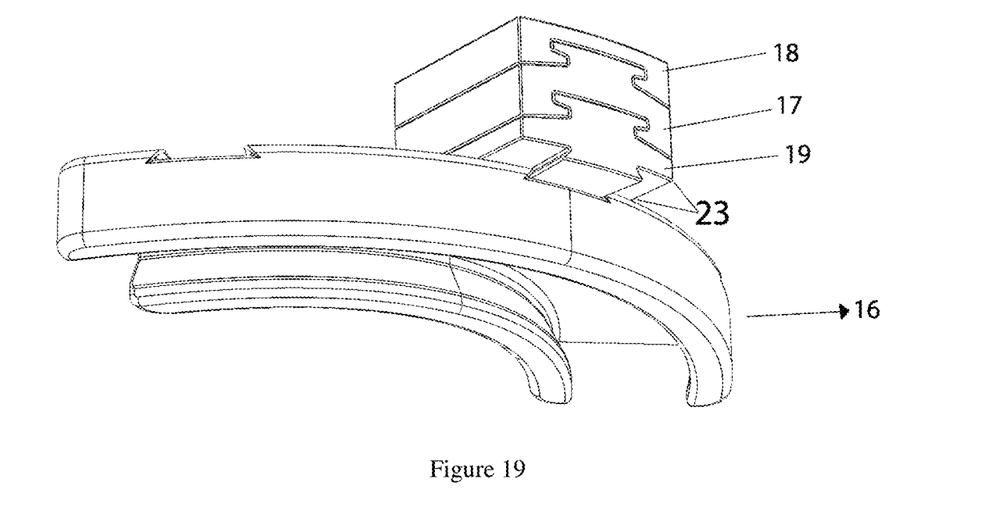
FIG. 19—Outside view of spacer (16) in bottom position with elements (17) (18) (19) fitted in central position showing projection (23).
Figure 20:
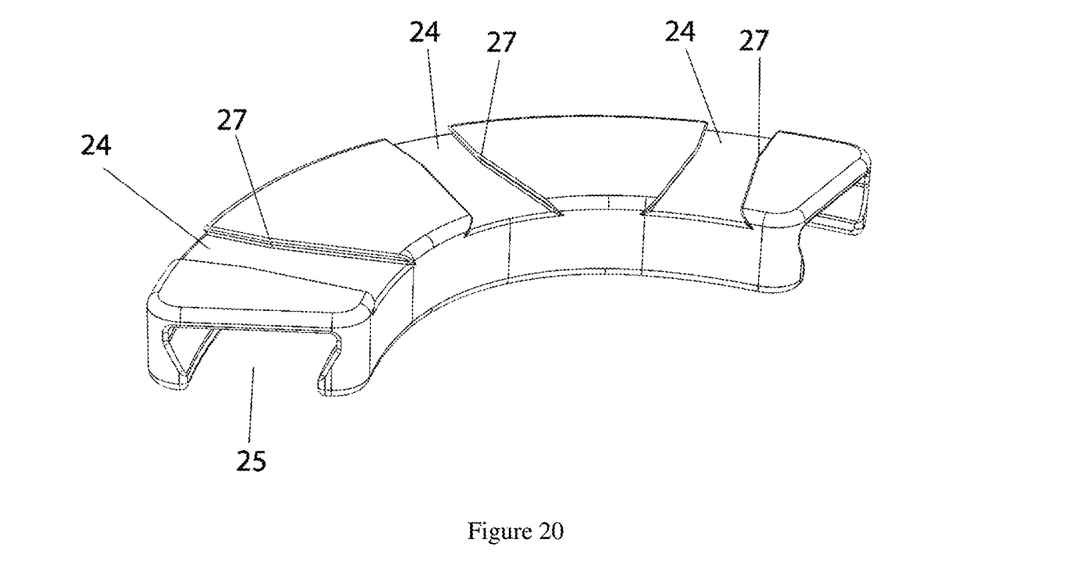
FIG. 20—Spacer (16) where slots (24) (25) are visible.
Figure 21:
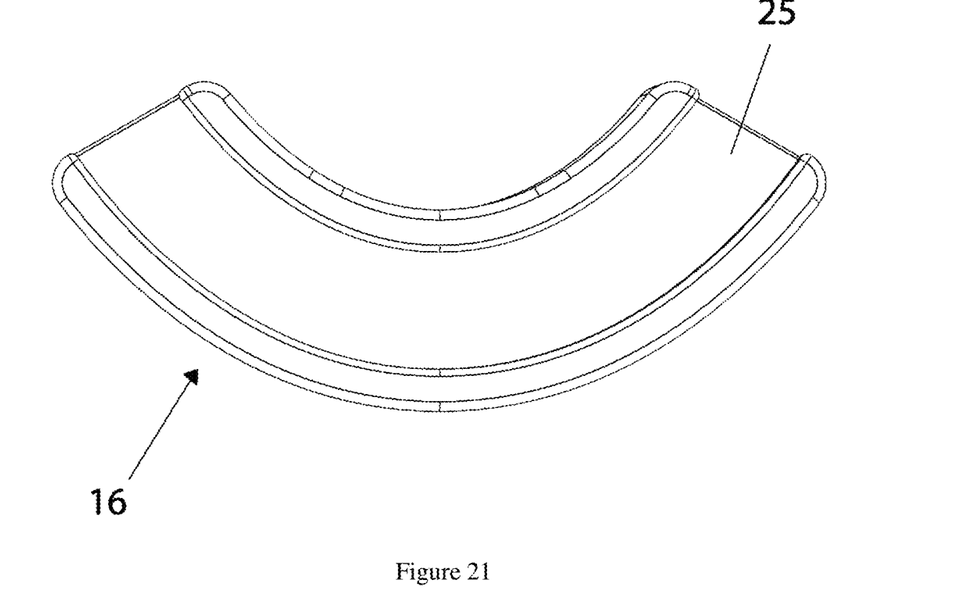
FIG. 21—Top view of groove (25) on spacer (16).
Figure 22:
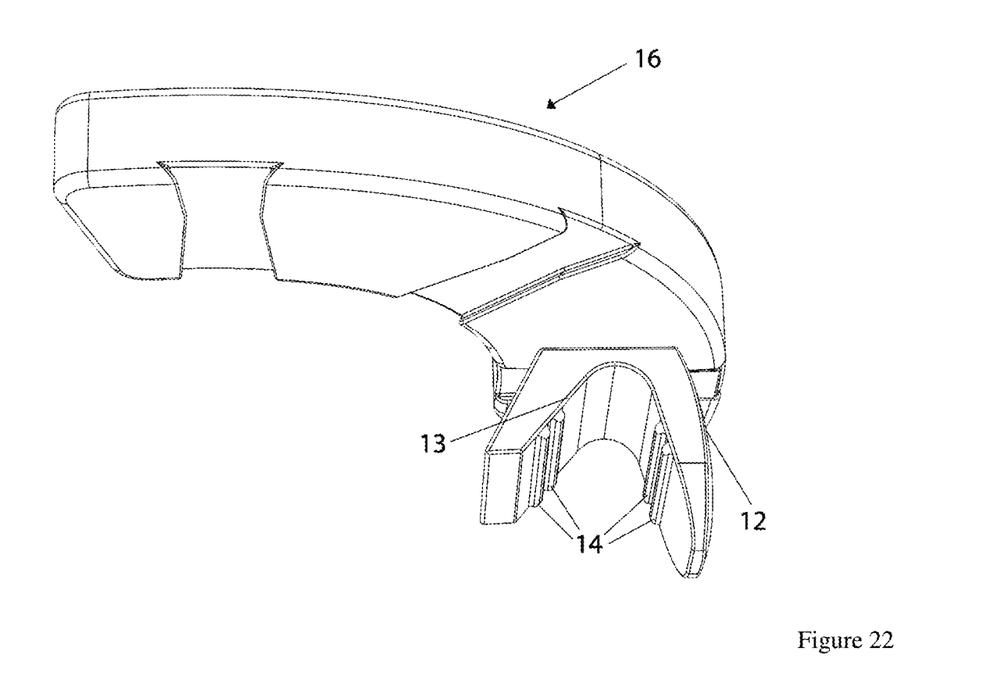
FIG. 22—Spacer (16) with marker (26) on upper left position.
Figure 23:
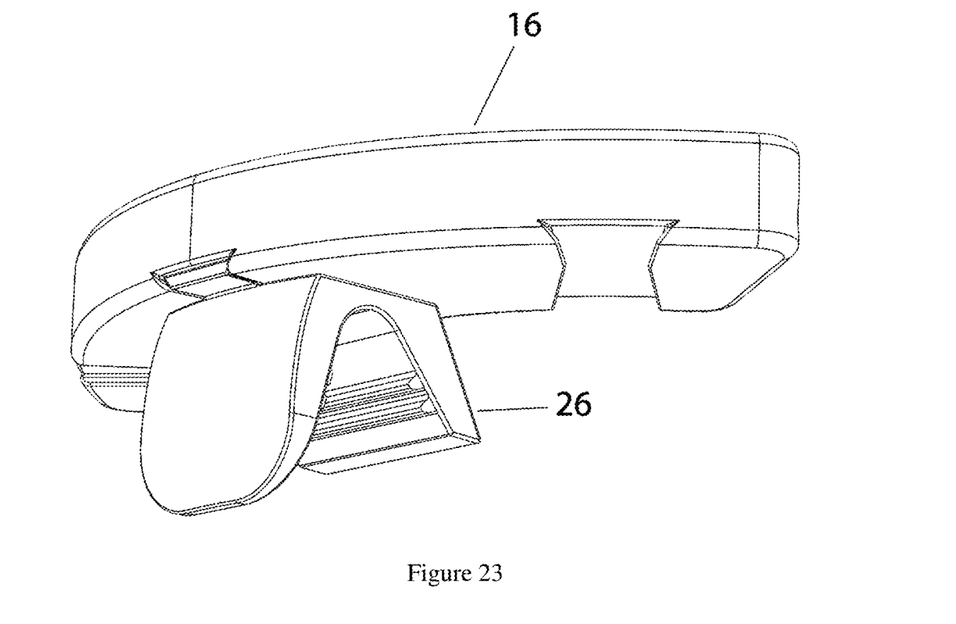
FIG. 23—Spacer (16) with marker (26) on upper central position.
Figure 24:
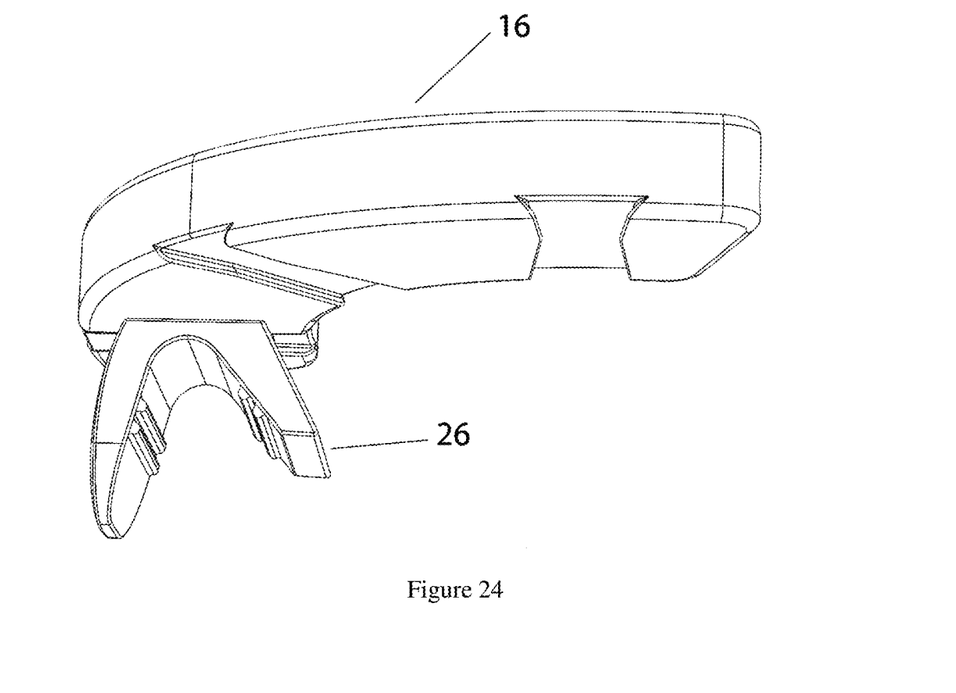
FIG. 24—Spacer (16) with marker (26) on upper right position.
Figure 25A:
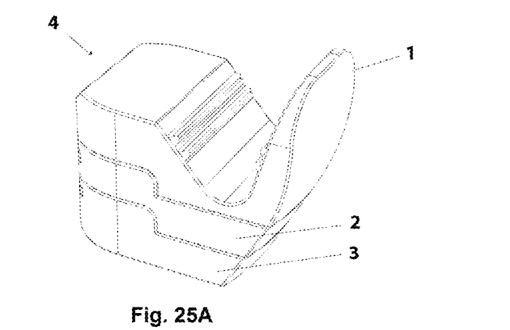
Figure 25B:
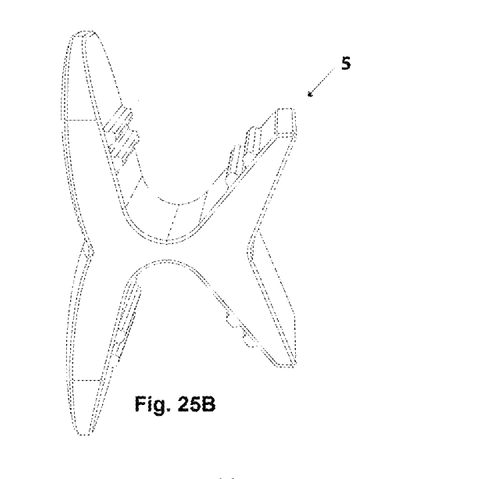
Figure 25C:
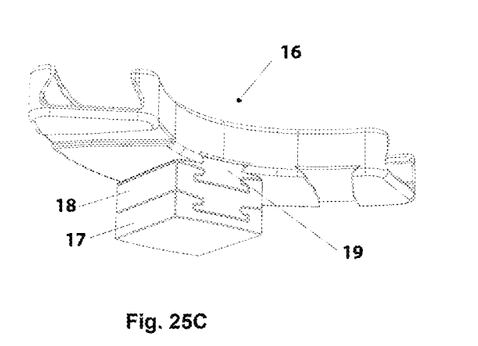
Figure 25D:
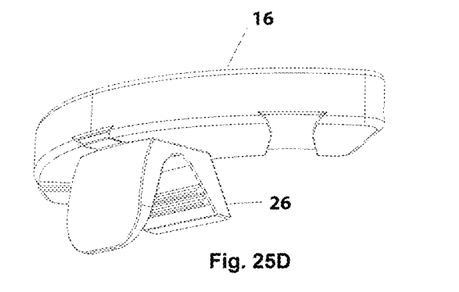

To determine individual values, the following reference positions are recorded, and represented in FIG. 7:

protrusive (FIGS. 7A-1 through 7A-4)—the marker (5) is placed and stabilized on incisors in order to achieve an intermaxillary relation close to edge to edge position and scans are made to register the lateral separation space between the dental arches;

right laterotrusive (FIGS. 7B-1 through 7B-4)—the marker (5) is placed and stabilized on right side canines, in order to achieve an intermaxillary relation close to alignment of canine cusps on the same side and scans are made to register the lateral separation space between the dental arches;

left laterotrusive (FIGS. 7C-1 through 7C-4)—the marker (5) is placed and stabilized on left side canines, in order to achieve an intermaxillary relation approximate to alignment of canine cusps on the same side and scans are made to register the lateral separation space between the dental arches;

It should be noted that the three mentioned measurements are performed using the intraoral scanner.

The marker (16) is designed to stabilize elements in situations where patients have no teeth in the incisors and/or canines positions. In this situation, the measurements are made with aid of elements (17) (18) (19) and marker (26) which have the same role of elements (1) (2) (3) and marker (5), respectively.

BRIEF DESCRIPTION OF THE FIGURES

FIG. 25—Set of representations of the present invention, FIG. 25A, FIG. 25B. FIG. 25C and FIG. 25D, already represented in the above figures.

DETAILED DESCRIPTION OF THE INVENTION

This invention consists of a set of three-dimensional markers that should be included in the virtual face-bow transference. These markers together with the dental arches scanned information allow the transposition to the virtual articulator, of axiography and the determination of individual values for virtual articulators. The invention is described by:

marker (4) which has three interchangeable parts: upper element (1)—3 mm thick, intermediate element (2)—2 mm thick and the lower element (3)—1 mm thick. The elements fit together, allowing different combinations and creating a single piece (4);

marker (5).

Marker (4) has three elements (1) (2) (3), which have slots and projections, through which the elements can attach to each other.

It is important to define the directions front, rear, upper, lower and lateral, to the clarifying and well understanding of the different features of the invention when the markers are placed in the teeth:

front area—area of the markers that stays, outside the mouth (more specific between the teeth's and the lips);

rear area—area of the markers that stays inside the mouth;

upper—area of the markers nearest to the palate;

lower—area of the markers opposite to the upper area;

lateral—area of the markers between the upper area and the lower area.

Both lower (3) and intermediate (2) elements have two projections (6) (7) in the lateral upper rear area. The front area is the one facing outwards when placed in the mouth and the rear area is the one that lies inside the mouth.

Intermediate (2) and upper (1) elements have two hollows (8) (9) in the lateral lower rear area, where the projections (6) (7) fit through sliding. This way, the elements (1) (2) (3) are fixed and the marker (4) becomes a single piece.

The three elements (1) (2) (3) have a rear semi-elliptical shape and a front flat shape. The element (1) has a projection (10) in the upper front area that must be aligned with the buccal face of upper incisor. This projection has a slot formed by two ridges (14) on the inner sides to create retention with the stabilizing material (waxes, impression compound or elastomers) and to be fixed so the measurements can be accurate. The projection (10) develops into a depression (11) where the edges of the maxillary incisors will be positioned. The rear elevation area also has a slot formed by two ridges (14) on the inner side, with the same purpose of retaining the stabilization material.

The element (1) has a tilted cut (15) at the inner end area so that there are no sharp edges that could injure the patient.

The marker (5) has a two-part symmetric geometry, each one formed by a projection (12) that will be positioned outside the buccal surfaces of the teeth. This projection has a slot formed by two ridges (14) on the inner side to provide retention of the stabilization material (waxes, impression compound or elastomers) and to support the attachment so that measurements are accurate. The projection (12) develops into a depression where teeth will be standing. This projection gives rise to a second projection (13) representing the rear area which also presents a slot formed by two ridges (14) on the inner side with the same purpose of providing retention of the stabilizing material. This rear zone should be aligned into the lingual surfaces of teeth.

The purpose of spacer (16), elements (17) (18) (19) and the marker (26) is to determine the individual values in cases where the patient has no teeth in the positions of the incisors and/or canines.

The spacer (16) is designed in a way to restore the shape integrity of dental arches, preferably semi elliptical arcs. One of the parts, the bottom one if the spacer is being placed on the lower jaw or the upper part if the spacer is positioned in the upper jaw, presents a groove (25) across its surface. This groove enables the fixation to soft tissues or to auxiliary placement components when dental implants are present. The opposite side has three slots (24) which allow the marker (26) and the element (19) to fit in the correct positions for inter arches digitization.

Additionally, the slots (24) have a lower dimension on the outside of the spacer (16) than the dimension shown on the inside of the spacer (16). In fact, the slots (24) show a narrower area starting at point (27). This not only allows marker (26) to fit in the correct position, but also permits element (19) to fit so that its engagement with the remaining elements (17) and (18) show the projection (23) to the outside.

With respect to function, the elements (19), (17) and (18) correspond to the elements (1), (2) and (3) respectively, but with different geometric configurations in order to be fixed to spacer (16) and not directly on the patient's teeth.

Therefore, the element (19) has an top fit (28) geometrically identical to the slots (24). One end of the top fit (28) has the same length of slot (24) at point (27) so that it remains fixed in this position. This top fit (28) determines that the element (19) also presents two lateral projections (20). The element (19) has two protrusions (22) at the bottom which will fit the element (17).

The element (17) presents a slot (29) on top which creates two engagements (21) that fit with the projections (22) of element (19). This way, they will be connected and fixed to each other. At the bottom, the element (17) has the same two protrusions (22), which this time will fit into element (18).

The element (18) has a top slot (29) which creates two engagements (21) that fit the projections (22) of element (17). This way, they will be connected and fixed to each other. The element (18) is flat at the bottom surface.

The marker (26) is similar to the marker (5) but only includes one symmetry part. Thus, it only has one projection (12) which will be placed outside the buccal surfaces of teeth and presents a slot formed by two ridges (14) on the inner lateral side to provide retention for stabilization material (waxes, impression compound or elastomers) and to support the attachment so that measurements are accurate. The projection (12) develops into a depression where teeth will fit. This projection raises a second projection (13) that is the rear part and which also presents a slot formed by two ridges (14) on the inner lateral side with the same purpose of retaining the stabilizing material. This rear part must be aligned inside of the lingual faces of teeth.

The invention claimed is:

1. A set of three-dimensional markers for intra-oral dental scanning comprising:
   a first marker to provide a reference for locating a mandibular closure arch, comprising
   an upper element, an intermediate element, and a lower element, which fit together to form a single part;
   said upper element comprising
   a rear area having a tilted cut,
   a first alignment projection in an upper front area developing into a depression for positioning adjacent to maxillary incisors, and
   first retention slots formed by ridges for retaining stabilizing material;
   said intermediate element located between said upper and lower elements;
   said intermediate and upper elements each comprising a lateral lower rear area with at least two slots;
   said intermediate and lower elements each comprising a lateral upper rear area with at least two projections, said at least two projections fitting into said at least two slots by sliding;
   a second marker for positioning outside buccal surfaces, the second marker having a second alignment projection and second retention slots formed by ridges for retaining stabilizing material;
   a third marker for use in edentulous patients, comprising
   an upper element, an intermediate element, and a lower element, which fit together to form a single part;
   said intermediate and upper elements each comprising bottom projections;
   said intermediate and lower elements each comprising top slots, said top slots fitting into said bottom projections by sliding;
   said upper element comprising a top projection; and
   at least one spacer for restoring a shape of a dental arch, wherein said at least one spacer is configured to be positioned adjacent to said second marker or to said upper element of said third marker,
   wherein
   said upper front area denotes an area of said markers that remains outside the patient's mouth, between the patient's teeth and lips;
   said rear area denotes an area of said markers that remains inside the patient's mouth;

said upper rear area denotes an area of said markers inside the patient's mouth adjacent to the patient's palate, and said lower rear area denotes an area opposite to the upper rear area.

2. The set of three-dimensional markers according to claim 1 wherein said stabilizing material is selected from a group consisting of impression compound, waxes, and quick-set elastomeric material.

3. The set of three-dimensional markers according to claim 1 wherein said upper, intermediate, and lower elements of said first marker have a semi-elliptical shape.

4. The set of three-dimensional markers according to claim 1 wherein said at least one spacer has a semi-elliptical arc configuration.

5. The set of three-dimensional markers according to claim 1 wherein said upper, intermediate, and lower elements of said first marker have thicknesses in a range of one to three millimetres.

* * * * *